US006599477B1

(12) United States Patent
Miyake et al.

(10) Patent No.: US 6,599,477 B1
(45) Date of Patent: Jul. 29, 2003

(54) CHEMICAL ANALYSIS APPARATUS (75) Inventors: Ryo Miyake, Tsukuba (JP); Akira Koide, Ibaraki-ken (JP); Takeo Takagi, Tsukuba (JP); Takao Terayama, Ushiku (JP); Yasushi Nomura, Mito (JP); Hiroshi Mitsumaki, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/136,070

(22) Filed: Aug. 19, 1998

(30) Foreign Application Priority Data

Aug. 20, 1997 (JP) ............................. 9-223334

(51) Int. Cl.⁷ .................... G01N 35/04; G01N 35/02
(52) U.S. Cl. .................... 422/64; 422/63; 422/67; 422/100; 422/103; 422/104; 436/43; 436/47; 436/49; 436/54; 436/180; 414/416.05
(58) Field of Search ............... 422/63, 64, 67, 422/100, 103, 104; 436/43, 47, 49, 54, 180; 417/416.05

(56) References Cited

U.S. PATENT DOCUMENTS

| | | | | |
|---|---|---|---|---|
| 4,346,056 A | * | 8/1982 | Sakurada | 422/64 |
| 4,455,280 A | * | 6/1984 | Shinohara et al. | 422/63 |
| 4,844,868 A | * | 7/1989 | Rokugawa | 422/64 |
| 5,085,562 A | * | 2/1992 | Van Lintel | 417/413 |
| 5,173,741 A | | 12/1992 | Wakatake | |
| 5,232,664 A | * | 8/1993 | Krawzak et al. | 422/64 |
| 5,336,062 A | * | 8/1994 | Richter | 417/413 A |
| 5,424,036 A | * | 6/1995 | Ushikubo | 422/64 |
| 5,529,465 A | * | 6/1996 | Zengerle et al. | 417/413.2 |
| 5,654,200 A | * | 8/1997 | Copeland et al. | 436/46 |

FOREIGN PATENT DOCUMENTS

| | | |
|---|---|---|
| DE | 4405004 | 2/1994 |
| DE | 4422743 | 6/1994 |
| DE | 19648695 | 11/1996 |
| EP | 299662 | 7/1988 |
| EP | 431352 | 11/1990 |
| EP | 556566 | 1/1992 |
| EP | 618426 | 3/1994 |
| EP | 703364 | 8/1995 |
| EP | 725267 | 1/1996 |
| EP | 753746 | 7/1996 |
| WO | 8300932 | 3/1983 |
| WO | 9612561 | 5/1996 |

OTHER PUBLICATIONS

Patent Abstracts of Japan C–1166 Reb. 1994 vol. 18, No. 93 & JP–5–293391.
Patent Abstracts of Japan P–1776, Jul. 1994, vol. 18, No. 399 & JP–6–117969.

* cited by examiner

*Primary Examiner*—Jill Warden
*Assistant Examiner*—Kathryn Bex
(74) *Attorney, Agent, or Firm*—Antonelli, Terry, Stout & Kraus, LLP (57) ABSTRACT

A chemically analyzing apparatus includes a plurality of reaction containers, a reaction container holder for holding the plurality of reaction containers and for supplying a sample and reagent at predetermined positions, a plurality of reagent containers for holding reagent adapted to be supplied into the reaction containers, a reagent container holder provided above the reaction container holder, for holding the plurality of reagent containers, a measuring part for measuring physical properties of the sample, a liquid feed mechanism provided in a lower part of each of the plurality of reagent containers, for supplying a predetermined quantity of reagent from each of the reagent container into the associated reaction containers by means of the liquid feed mechanism. With this arrangement, it is possible to provide a chemically analyzing apparatus incorporating a reagent supply mechanism which can prevent reagent from being uselessly consumed, which does not substantially require washing liquid, which does not require periodical disassembly and washing, and which can easily change the feed quantity of reagent.

8 Claims, 7 Drawing Sheets

CHEMICAL ANALYSIS APPARATUS

The present invention relates to a chemically analyzing apparatus for quantifying a density of a substance dissolved in liquid, and in particular to a chemically analyzing apparatus for analyzing a component such as biological fluid or the like.

Conventionally, as to a reagent supply mechanism in a chemically analyzing device, a reagent pipetting mechanism as disclosed in U. S. Pat. No. 4,451,433, and a dispenser mechanism composed of a syringe pump, a flow selector valve and a reagent discharge nozzle have been used.

The above-mentioned reagent pipetting mechanism having a structure and performing the operation which are explained in detail in the above-mentioned U. S. Patent, requires a relatively long time for three-dimensionally moving a nozzle and washing thereof, and accordingly, it can only carry out a limited number of tests per unit time. However, it is suitable for analyzing several kinds of test items.

Further, the above-mentioned dispenser mechanism has a selector valve which is connected thereto with several oncoming tubes from reagent containers, and which is also connected thereto with outgoing tubes in the same number as that from the reagent containers. In addition, the selector valve is connected thereto with a tube communicated with a syringe pump for controlling the flow of reagents. At first, the reagents are filled in the tubes between the reagent containers and the selector valve and tubes between the selector valve and reagent discharge nozzles. In this initial condition, in order to discharge a desired reagent, the selector valve is operated so as to communicate a tube from the corresponding reagent container with the syringe pump which effects suction so as to draw up a predetermined volume of the desired reagent into the tube on the syringe pump side through the selector valve. Then, the selector valve is again operated so as to connect the tube between the syringe pump and the selector valve with a tube between the selector valve and associated one of the reagent discharge nozzles. In this condition, the syringe pump discharges the reagent by a predetermined quantity into a reaction container from the tube. Accordingly, this mechanism can perform the change-over and supply of reagents at a high rate. However, this mechanism is not suitable for being used in such a case that several kinds of reagents are used since the reagent discharge nozzles should be provided by a number equal to the number of kinds of reagents to be used. Rather, this mechanism is suitable for test item such that the number of kinds of reagent is small, but the number of tests is large.

Conventionally, an automatic analyzing apparatus having a piston mechanism is disclosed in Japanese Laid-Open Patent No. S63-131066. This apparatus is at first aim at decreasing the size thereof by overlapping the moving locus of a holder for holding a reagent container with that of a holder for holding a reaction container. A reagent is discharged by a piston integrally incorporated with a side wall of the associated one of the reagent containers. The piston is driven by a piston rod drive device provided at a discharge position of the reagent. At this discharge position, the piston rod drive device associated with this reagent container is transitorily connected to the piston. Then, the piston is lifted up by the piston rod drive device so as to suck the reagent into the piston from the reagent container. When the piston comes up to the uppermost position, the piston is meshed with a gear for rotating the piston, and accordingly, the piston is turned by an angle of 180 deg. by this gear. In this phase, a hole which has been opened for sucking the reagent is closed through the rotation of the piston while a hole communicated with a discharge port is opened. When the piston is moved down, the reagent is discharged into the reaction container from the piston through the hole as mentioned above.

The conventional above-mentioned reagent supply mechanism has offered the following disadvantages.

First, the reagent is uselessly consumed by a certain quantity. That is, in order to prevent the reagent sucked in a nozzle from being mixed with pure water, an air layer is defined between the reagent and the pure water. However, the water would go along the inner wall of the nozzle and be inevitably mixed with the reagent in the upper part of the latter. Accordingly, in order to prevent the reagent mixed with the water from being used for analysis, the reagent is sucked into the nozzle by a quantity which is greater than a quantity actually required for analysis by about 30%. The reagent to be used for the analysis is very expensive, and accordingly, such an extra quantity of the reagent causes the inspection cost to uselessly increase.

Second, it requires a long time and a much volume of liquid for washing. That is, in order to prevent reagents from being mixed with one another through the nozzles, the interior and the exterior of the nozzle are washed every time with washing liquid, and accordingly, a larger volume of the washing liquid and a longer washing time are required.

Third, residue is more or less left even though the interior and the exterior of the nozzle are washed by the washing liquid, and accordingly, errors in measured values are inevitably caused.

In the case of a reagent dispenser mechanism, the following two disadvantages are caused:

First, the reagent is uselessly consumed similar to that mentioned above. In order to rapidly discharge any one of reagents, all reagents are previously filled in tubes connecting the reagent containers to a selector valve and tubes connecting the selector valve to discharge ports. The reagents charged in these tubes are uselessly discarded when the apparatus is stopped. In some cases, the reagent is discarded by a quantity corresponding to that for more than 100 persons although it depends upon kinds of the reagents, and the lengths of the tubes.

Second, the maintenance for the selector valves is troublesome. That is, various kinds of the reagents pass through the selector valve one by one, and accordingly, the selector valve becomes gradually contaminated. In some cases, a valve element would stick to a valve seat since various kinds of reagents make contact with each other. Thus, it is required to periodically disassemble and wash the selector valve.

In the case of a piston type as a third example, the reagent is consumed by a less quantity in comparison with any of the above-mentioned examples. However, since the reagent still remains in a passage extending from a reagent container to a tip end of a pipetter even after the apparatus is shut down, and accordingly, the reagent in that part is uselessly discarded. Further, although the quantity of the reagent to be fed has to be changed, depending upon a density of a sample, it is impossible to discharge the reagent by a volume other than that previously set due to a fixed distance of reciprocation of the piston since the position of a gear provided in the upper part of the piston, for rotating the same, is fixed. Further, since the piston is provided to one side surface of the associated container, it is required to pump up the reagent up to a position which is higher than the position of the reagent container. Further, a pressure loss through the passage extending from the reagent container to the tip end of the pipetter is not negligible. Accordingly, a pressure should be applied more or less, and accordingly, the drive mechanism for the piston becomes complicated and large-sized. That is, the use of a simple and small-sized pump has been hindered.

As mentioned above, any one of conventional reagent supply systems offers a problem of consumption of useless reagents. Further, the reagent pipetting mechanisms requires a large quantity of washing liquid in order to prevent contamination between reagents. Further, the reagent dispensing mechanism requires troublesome disassembly and washing. Further, the piston system cannot supply a reagent only by a predetermined quantity. Alternatively, it has a complicated structure.

Further, Japanese published PCT Application (Published Japanese Translation of PCT application) No. H6-510582 discloses an example of conventional micropumps for discharging a slight quantity of reagent or the like. This micropump is a static-electrically driven diaphragm micropump which includes a first pump body having conductive electrode zones electrically connected to a voltage source and electrically insulated from one another, a second pump body provided therein with a diaphragm area, and a pump chamber incorporating a flowing direction control means having a resistance depending upon a flowing direction of drawn-up fluid, and in which two pump bodies define therebetween a hollow space making contact with the diaphragm area and filled therein with fluid medium spatially separated from fluid drawn up, and the conductive electrode zones of the pump body are arranged so that the fluid medium is subjected to electric fields produced between the above-mentioned conductive electrode zones while the drawn-up fluid is hardly subjected to the electric fields. In this conventional structure, the diaphragm is deformed by static electricity for drawing up liquid, and then, the static electricity is removed so that the diaphragm exhibits its restoring force with which the liquid is discharged.

However, the conventional static-electrically driven micropump as mentioned above, is the one for discharging liquid into liquid. However, this device has offered a problem such that the characteristic of liquid discharge into gas in the case of an inkjet printer or a biochemical automatic analyzing device in which a reagent is discharged, or the like, is inferior, and accordingly, which has not yet been practically developed. Thus, inkjet printers of a piezoelectric disc type, evaporating type or the like, which are expensive have been prosperously used, and further, biochemically analyzing devices of the piezoelectric type or the like have hardly been used since their costs are high and their reliability is low.

The above-mentioned problems of the static-electrically driven discharge micropump are caused by such a fact that liquid is sucked up through the electrostatic deformation of the diaphragm, and is discharged by the restoring force of the diaphragm which is effected for allowing the diaphragm to take its original shape when the static electricity is removed. Accordingly, the diaphragm is designed to have a high degree of rigidity. However, when the diaphragm is deformed through the application of the static electricity so as to store a force, the discharge pressure becomes soon lower as the degree of deformation of the diaphragm becomes small even though the discharge pressure is high upon initiation of the discharge. Thus, the static electricity can not be used satisfactorily, that is, the efficiency is low. For example, in the case of the application of this pump for discharging a reagent in a biochemically analyzing apparatus in which liquid is discharged into gas, or the like, the stream of the reagent has less momentum so that the sensitive operation of a discharge nozzle part cannot be expected, and accordingly, residual liquid drops are present in the discharge nozzle part, thereby satisfactory discharge with a high degree of reproducibility can hardly be expected.

OBJECT AND SUMMARY OF THE INVENTION

Accordingly, one object of the present invention is to provide a chemically analyzing apparatus incorporating a simple reagent supply mechanism (discharge device) which can prevent reagents from being uselessly consumed, and which does not require a substantial quantity of washing liquid and periodic disassembly and washing, and with which the quantity of a reagent can be simply changed.

To the end, according to the present invention, there is provided a chemically analyzing apparatus comprising a reacting container holder with which a sample and a reagent are fed at a predetermined position, for holding a plurality of reacting containers, a measuring device for measuring physical properties of the sample, a plurality of reagent containers having lower parts, and liquid feed means provided respectively in the lower parts of the reagent containers, being associated with the latter.

It is noted that each liquid feed means is provided therein with a pressing pin as a drive device for a diaphragm in a liquid feed chamber, and the pressing pin is driven at a predetermined speed in a direction substantially orthogonal to the diaphragm so as to press the diaphragm in the direction in which the volume of the liquid feed chamber is decreased in order to discharge the fluid from the liquid feed chamber.

DESCRIPTION OF THE PREFERRED EMBODIMENTS

Explanation will be hereinbelow made of an embodiment of a chemically analyzing apparatus according to the present invention, with reference to FIGS. 1a to 4.

Figure 1A:
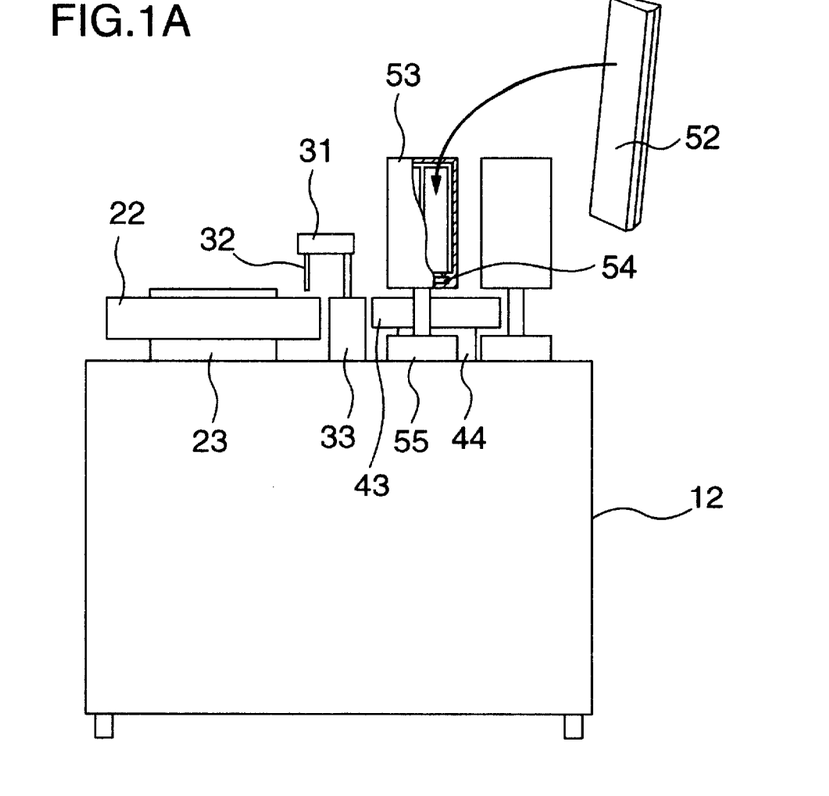
FIGS. 1a and 1b are front and top views illustrating a chemically analyzing apparatus according to the present invention.
Figure 1B:
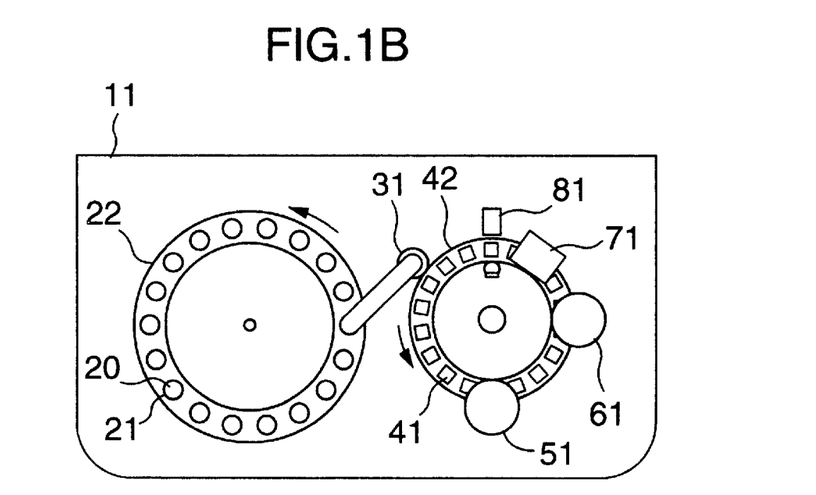

FIG. 1A is a front view which shows an apparatus 11, and FIG. 1B is a top view which show an apparatus 12.

A sample holder 22 for circumferentially holding test tubes 21 holding therein samples 20 is provided on the top surface of the apparatus. A sample pipetter 31 for sucking up the samples 20 from the test tubes 21 is provided on one side of the sample holder 22. The sample pipetter 31 is composed of a nozzle 32 for sucking up a sample and holding therein the same, a three-dimensional drive mechanism 33 for elevating and rotating the nozzle 33, and a pump which is not shown, for sucking up a sample into the nozzle 32 and discharging the sample from the nozzle 32.

The sample holder 22 is rotated by a rotary drive mechanism 23 in order to set one of the test tubes 21 in the sample holder 22 at a position just below the nozzle of the sample pipetter 31. Reaction containers 41 are successively moved through a position to which the nozzle of the sample pipetter 31 is lowered, while they are rotated.

The plurality of reaction chambers 41 are held on a reaction disc 42 along the periphery thereof. Each of the reaction containers defines in its lower half part a constant temperature chambers 43 through which water at a constant temperature flows. In order to successively move the reaction containers to the position at which the nozzle of the sample pipetter is lowered, the reaction disc 42 is supported by a disk rotating drive mechanism 44. In addition to the above-mentioned sample pipetter and the like, the reaction disc 42 is provided thereon with a first reagent supply part 51, a second reagent supply part 61, a reaction container washing mechanism 71 and a spectromeasuring part 81 which are arranged counterclockwise in the mentioned order, along the periphery of the reaction disc 42.

Figure 2:
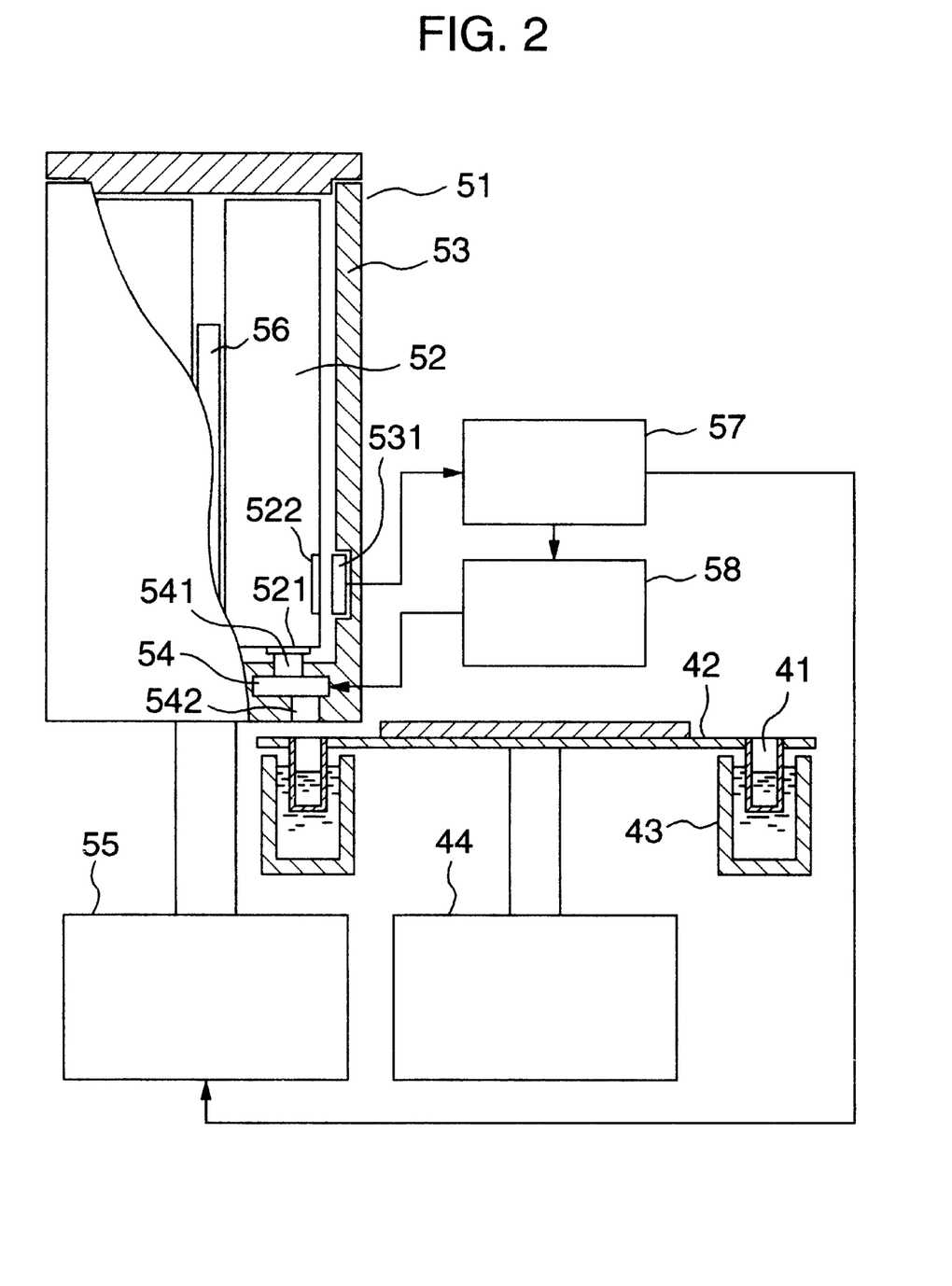
FIG. 2 is a partly broken diagramic view illustrating a reagent supply part according to the present invention.
Figure 3:
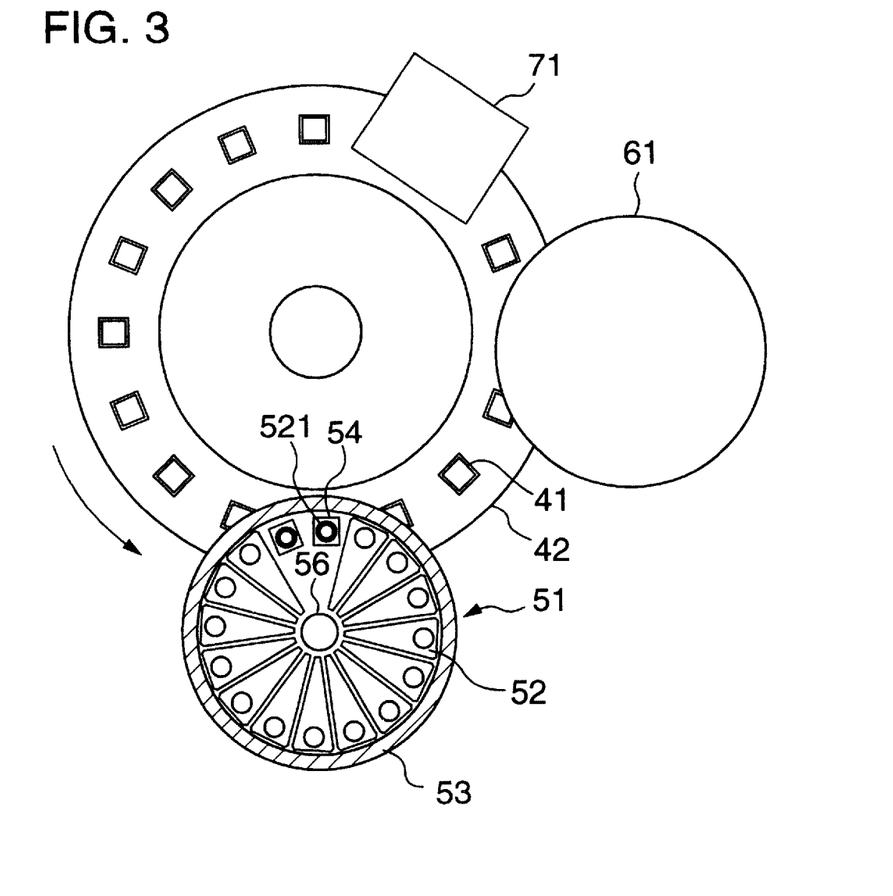
FIG. 3 is a top view illustrating the regent supply part shown in FIG. 2.

The structure of the first reagent supply part 51 will be explained in detail with reference to FIGS. 2 and 3. It is noted that the structure of the second reagent supply part 61 is the same as that of the first reagent supply part 51, and accordingly, the explanation of the second reagent supply part 61 will be omitted for brevity. Further, referring to FIG. 1, although two reagent supply parts are shown, only one reagent supply part may satisfy for performing the function of the apparatus. FIG. 2 is a detailed view which shows the reagent supply mechanism, and FIG. 3 is a top view which shows the reagent supply mechanism.

The reagent supply part 51 is mainly composed of four components, that is, a reagent container 52 and a reagent holder 53, a micropump 54, and a reagent holder rotating drive mechanism 55. The reagent holder 53 has a structure such as to circumferentially hold the reagent containers 52 around a center shaft 56. In this embodiment, the micropumps 54 of a membrane type having a number equal to that of the reagent containers 53 to be held are provided in the bottom part of the reagent holder 53. Further, in this embodiment, each of the reagent containers is formed in its bottom surface with a connection hole 521 which is connected with a suction port 541 of the associated micropump 54 when the reagent container 52 is firmly pressed toward the bottom part of the reagent holder 53.

The micropump 54 is formed therein with a discharge port 542 which is directed vertically so as to discharge liquid in the gravitational direction. The reagent container 52 is provided at its side surface with a magnetic recording part 522 on which data containing a kind of reagent are written. A magnetic reader 531 for reading data written on the magnetic recording part 522 is provided the reagent holder 53 at a position corresponding to the magnetic recording part 522. Instead of the magnetic recording part, a seal incorporating a bar code or the like may be applied to the side surface of the reagent container, and instead of the magnetic reader, a bar code reader may be used. Signal lines from the magnetic reader 531 are connected to a determining part 57 which is in turn connected to a micropump control part 58 which is adapted to drive the micropump 54. Further, the reagent holder is adapted to be rotated and shifted by the reagent holder rotating drive mechanism 55.

It is noted that the suction port of the micropump may be provided with a lid for opening and closing the connection port so as to prevent a reagent container being connected to the suction port of the micropump 54 even though it is firmly pressed if data read by the above-mentioned magnetic reader do not correspond to a kind of reagent which should be contained in the reagent containers 52 set in the reagent holder 53. Thus, it is possible to always set the reagent containers 52 containing therein the same kind of reagent on the reagent holder 53.

With this arrangement, it is possible to eliminate the necessity of washing of the reagent holder 53 and the micropump 54 each time when the reagent container 52 is replaced with another one.

Next, the structure of the micropump will be explained with reference to FIG. 4.

Figure 4:
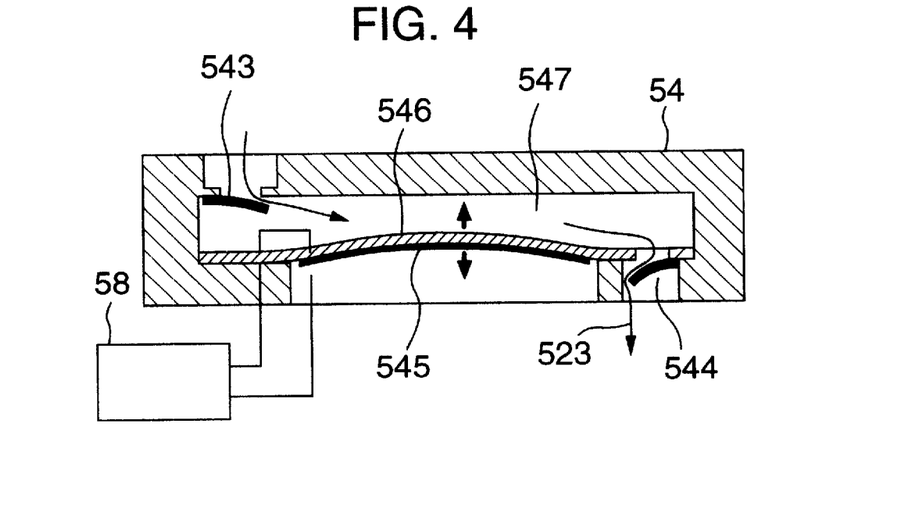
FIG. 4 is a sectional view illustrating a micropump incorporated in the reagent supply part shown n FIG. 2.

FIG. 4 shows the membrane type micropump in an embodiment of a liquid feed means incorporated in the reagent supply mechanism according to the present invention.

This micropump 54 is composed of an inlet valve 54, a pump chamber 547, a diaphragm 546, a vibrating panel 545, and outlet valve 544 which are arranged in the mentioned order from the inflow port to the discharge port. The vibrating panel 545 is connected with the micropump control part 58 through drive signal lines as shown in the figure. An a.c. signal is applied to the opposite surfaces of the vibrating panel 545 from the micropump control part 58 in accordance with a quantity of reagent to be discharged. Accordingly, the vibrating panel 545 is driven so as to warp in order to excite the diaphragm 546 by a predetermined frequency (corresponding to the quantity of reagent to be discharged).

Explanation will be hereinbelow made of the operation of the micropump having the above-mentioned structure.

At first, a predetermined quantity of the sample 20 is sucked from the test tube 21 into the nozzle 32 of the sample pipetter 31 which is the moved to the bottom of the reaction container 41 by the three-dimensional drive mechanism 33, and is discharged. The reaction container 41 is rotated and shifted to the reagent discharge position of the first reagent supply part 51 by means of the reaction disc rotating drive mechanism 43.

In the first reagent supply part, the reagent holder rotating drive mechanism is operated so that the discharge port 542 corresponding to a desired test item, is positioned just above the above-mentioned reaction container 41. At the time when the reaction container 41 and the discharge port 542 are positionally aligned with each other, a predetermined quantity of reagent is discharged into the reaction container by the micropump 54 under control of the micropump control part 58. If it is required to add second reagent, the reaction container 41 is rotated and shifted to the reagent discharge position of the second reagent supply part, and then the operation similar to that of the first reagent supply part is carried out.

Further, in order to add the third and fourth reagents, the reagent container is rotated once more, and is fed therein with them in the first and second reagent supply parts. When the supply of these reagents is completed, the reagents and the sample initiate gradual reaction with each other, and as a result, coloring is made corresponding to a density of a component in an item to be tested. The degree of the coloring corresponds to the density of the component. Since the degree of coloring corresponds to the density of the component, an absorption spectrum of a sample in the reaction container is measured by the spectromeasuring part so as to quantify the density thereof. After the measurement is completed, the sample in the reaction container 41 is sucked into the reaction container washing mechanism 71, and simultaneously, the inner wall of the reaction chamber is also washed.

The micropump 54 shown in FIG. 4 is operated as follows: At first, an a.c. signal is applied to both surfaces of the vibrating panel 545 from the micropump control part by a time corresponding to a predetermined frequency with which the vibrating panel 545 should be vibrated. Accordingly, the vibrating panel 545 warps so as to vibrate the diaphragm 546. When the diaphragm deforms downward, the inlet valve 543 is opened so as to suck the reagent 523 into the pump chamber 547, and then, when the diaphragm warps upward, the outlet valve 544 is opened so as to discharge the reagent 523 from the pump chamber. The quantity of the reagent discharged into the reaction container is proportional to the frequency of vibration of the vibrating panel 545, and is easily adjusted by the frequency of the exciting signal applied from the micropump control part 58.

It is noted that the internal volume of the micropump may be easily set to be less than 100 μL if a thin membrane type pump which has been manufactured by fully using a micromachining process is used as the micropump. Accordingly, it is possible to reduce the quantity of the reagent uselessly remaining in the micropump to a value less than 100 μL upon a shutdown of the apparatus. Further, since the pump in this embodiment is arranged in the bottom part of the reagent container, the reagent can be transferred simply downward, and accordingly, no extra pressure head is required, thereby it is possible to use a pump having a simple structure.

Figure 5:
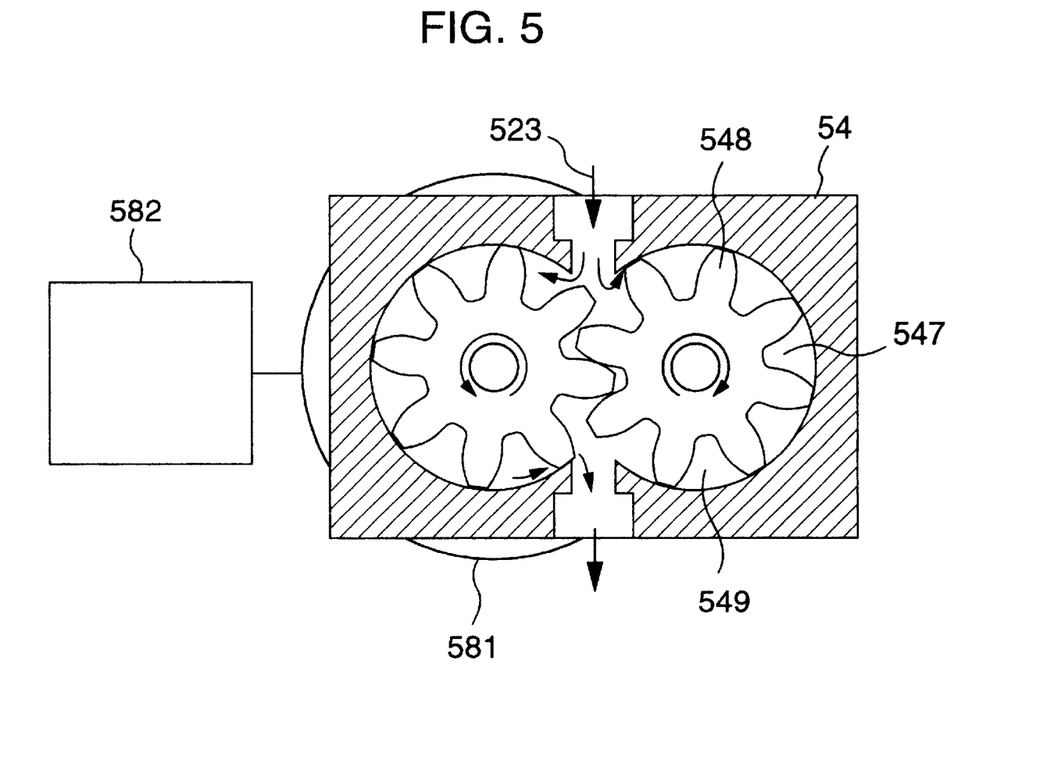
FIG. 5 is a sectional view illustrating a gear pump incorporated in the reagent supply part shown in FIG. 2.

Explanation will be hereinbelow made of an embodiment in which a gear pump shown in FIG. 5 is used as the micropump.

This gear pump incorporates two gears 548 which are meshed with each other in a pump chamber 547, and which are rotated in a direction indicated by the arrow in the figure, and accordingly, the reagent 523 sucked from the inlet port is confined in reagent holding chambers 549 defined between the gears 548 and the pump chamber 547, and is then fed to the outlet port. The reagent 523 held in two reagent holding chambers 549 are merged with each other at the outlet port before it is discharged from the outlet port. The gears 546 are rotated by a motor 581. The rotation of the motor is controlled by a motor control part 582.

In this embodiment, by setting a rotating angle of the gears, the quantity of the reagent fed into the reagent holding chambers 549 may be easily changed. Since the reagent is discharged in the gravitational direction, no extra pressure head is required, and accordingly, as shown in the figure, a pump which is small-sized and simple can be used. Further, due to the small-sized pump, the quantity of the reagent filled in the pump chamber can be set to be slight, and accordingly, the quantity of the reagent which must be uselessly discarded upon stopping of the apparatus, can become few.

As mentioned above, in this embodiment, in order to prevent carry-over between reagents, the micropumps 54 are provided exclusively for respective reagents. When the reagent container 52 is set in the reagent holder 53, data relating to a kind of reagent in the reagent container 52 are read from the magnetic part 522 provided at the side surface of the reagent container 52 by the magnetic reader 531. The determined part compares the data indicating the kind of reagent with data predetermined to the associated micropump, and if these data are coincident with each other, the micropump is driven soon so as to introduce the reagent into the micropump. However, they are not coincident with each other, an alarm is issued so as to transmit a signal to the micropump control part 58 in order to stop the drive of the pump. Thus, an accident of mixture of different kinds of reagent, which would occurs if a reagent container which contains a different kind of reagent would be set, can be prevented.

Figure 7:
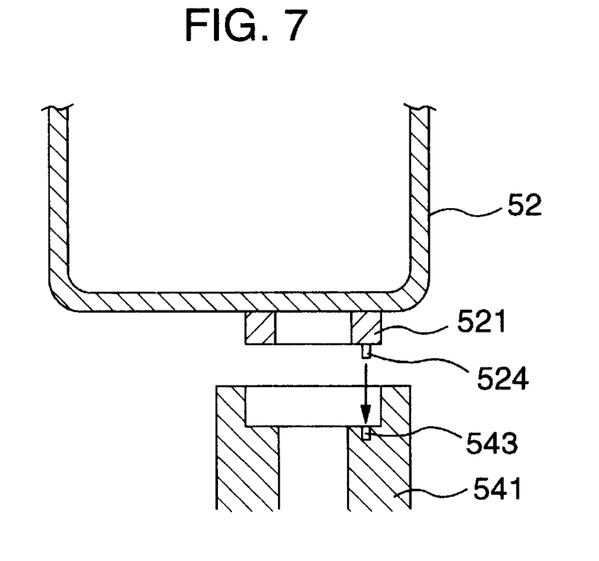
FIG. 7 is a sectional view illustrating a reagent container according to the present invention.

Referring to FIG. 7 which shows another embodiment that can prevent occurrence of erroneous connection between the reagent container and the reagent holder (or the pump), a protrusion 524 is provided in the vicinity of a connection port 521 of the reagent container, at a position which is different in accordance with a kind of reagent. A recess 543 is formed in the vicinity of the suction port 5 of the reagent holder 53, corresponding to the protrusion 542, at a position which is also different in accordance with a kind of reagent. Accordingly, only a reagent container which appropriately corresponds to the micropump can be connected, but other reagent containers cannot be connected. Thus, it is possible to prevent more than two kinds of reagents from flowing through one and the same micropump.

If the micropump 54 is not exclusively used for each one of the kinds of reagent, a system for feeding washing liquid to the micropump at a suitable time after the reagent container is removed, is provided. The washing liquid is fed into the suction port 541 of the micropump, although it is not shown, and thereafter, the interior of the micropump can be washed through the liquid feed action of the micropump itself. Thus, it is possible to prevent carry-over between the reagents.

According to the above-mentioned embodiments, the reagent is filled in the micropump having a slight volume from the reagent container in order to supply the reagent into the reaction container. Accordingly, the volume of useless consumption of the reagent which is discarded after the apparatus is stopped, can be substantially eliminated. Further, the micropumps are exclusively used for respective kinds of reagents, and accordingly, it is not required to wash them each time when the reagent is fed. Thus, the necessity of the time and the washing liquid therefor can be eliminated. Further, the necessity of maintenance for a selector valve can be also eliminated.

Figure 6:
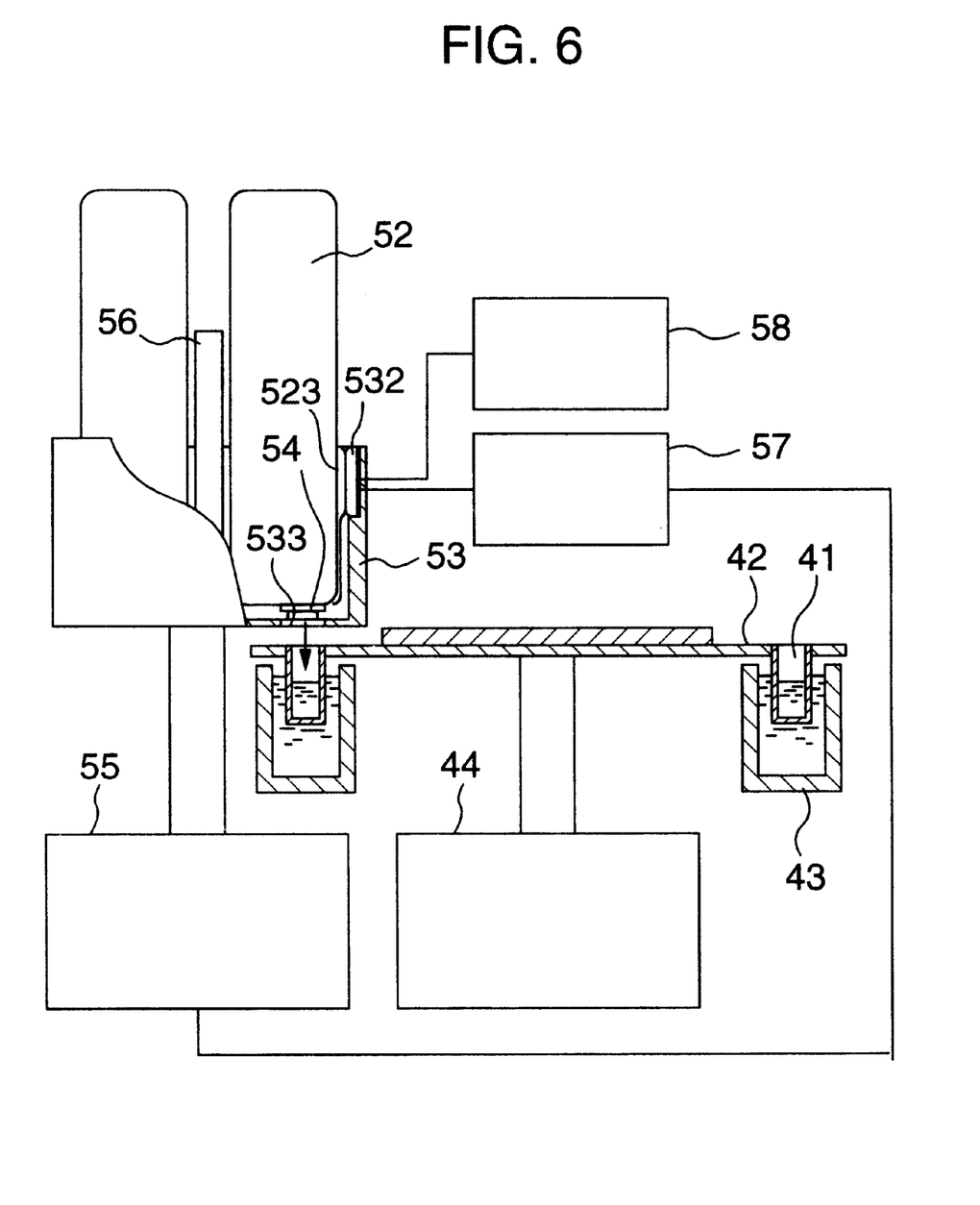
FIG. 6 is a partly broken diagram view illustrating a reagent supply part in another embodiment of the present invention.

Referring to FIG. 6 which is a view illustrating another embodiment of the present invention, a micropump 54 is directly provided to the bottom part of each of the reagent containers 52. When the reagent container 52 is inserted into the reagent holder 53, a signal connector 523 provided at the outer surface of the reagent container 52 is made into contact with a signal connector 532 provided at the side surface of the reagent holder 53 so that a drive signal for the micropump can be transmitted. The signal connector 532 is connected to the micropump control part 58. Further, the signal connector 523 is recorded in part thereon with data indicating a kind of reagent so as to set the kind of reagent on the determining part 57 when the signal connector is made into contact with the signal connector 532. The reagent holder 53 is formed in its lower part with a cut-out 533 having a relatively large size, for preventing the flow of the reagent discharged from the pump from being obstructed.

Data read through the signal connector 532 and relating to a kind of reagent are those previously recorded in the determining part 57, and accordingly, a designated reagent container is shifted to a position just above the reaction container. The micropump attached to the reagent container 52 starts its operation in response to an operation signal from the micropump control part 58, and accordingly, the reagent is discharged directly from the reagent container 52 into the reaction container 41.

In this embodiment, since the reagent does not make contact with any part of the apparatus body such as the reagent holder, completely no contamination occurs between reagents. The reagent in the reagent container can be fully used up to a portion filled in the micropump 58 without being uselessly consumed.

As mentioned above, the reagent container 52 and the reagent holder 53 are driven by the reagent holder rotating drive mechanism 55 provided in the lower part of the apparatus body. There may be provided a drive mechanism in the upper part of the apparatus so as to hold the reagent holder in a suspended condition. The reagent container may be moved not only through rotation but also parallel motion. Similarly, the reaction containers may, of course, be also moved through parallel motion in view of such a fact that different reaction containers are successively located at the reagent supply position although the reaction container is rotated and shifted in the present embodiment.

Further, in this embodiment, there are provided two reagent supply parts, but only one reagent supply part may, of course, be provided. Further, more than three reagent supply parts may be provided in view of kinds of reagents to be added. The reagent supply part according to the present invention may have a structure composed of a sufficiently simple structure in comparison with the conventional one, and accordingly, it is possible to easily provide more than tree reagent supply parts.

Figure 8:
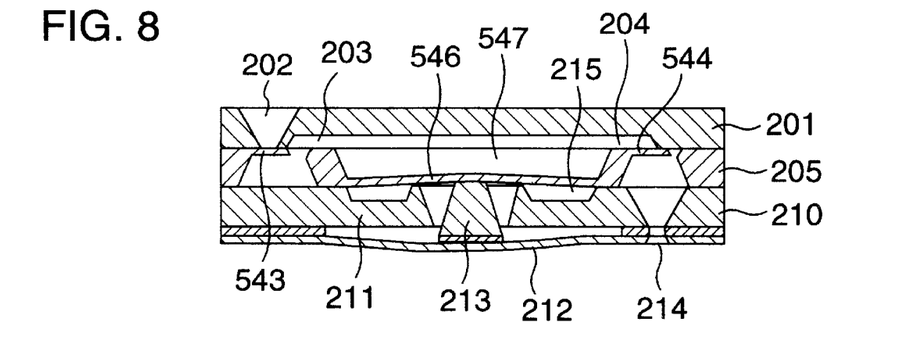
FIG. 8 is a sectional view illustrating a micropump in another embodiment of the present invention.

Then, explanation will be made of another arrangement of the micropump 54 as mentioned above. FIG. 8 shows another embodiment of the micropump.

The liquid feed chamber 547 is defined by joining a first liquid feed substrate 201 and a second feed substrate 205 with each other, and an inlet port communicated with the liquid feed chamber 547 is composed of a fluid introduction port 202 and an inlet passage 203 formed in the first liquid feed substrate 201, and an inlet valve 543 formed in the second liquid feed substrate 205 and serving as an inlet fluid resisting element, and an outlet port is composed of an outlet passage 20 formed in the first liquid feed substrate 201, and an outlet valve 544 formed in the second liquid feed substrate 205 and serving as a outlet fluid resisting element.

Further, the liquid feed diaphragm 546 is driven by a drive part composed of a stationary electrode 211, a movable electrode 212, a pressing pin 213, a resistance restraining groove 215 and a discharge nozzle 214, The first liquid feed substrate 210, the second liquid feed substrate 205, a stationary electrode substrate 210 and a movable electrode 212, and the pressing pin 231 are all joined together, being integrally incorporated with one another. However, it is not absolutely necessary to join the pressing pin 213 to the liquid feed diaphragm 546.

Further, the stationary electrode 211 and the movable electrode 212 are joined together through the intermediary of an insulating membrane interposed therebetween. As to the technology for joining these parts, a diffusion joining technology using an intervening metal thin film, a surface-active joining technology, a low melting point glass joining technology using an intervening lead glass pane, an anode joining technology using an intervening Pyrex glass pane, and a silicon direct joining technology in which silicon plates are directly joined or through the intermediary of a silicon oxide film, or the like may be used.

The liquid is fed as follows: when a voltage is applied between the stationary electrode 211 and the movable electrode 212 which are jointed through the intermediary of the insulating film 220, an static-electric force is generated between both electrodes so as to attract the movable electrode 212 toward the stationary electrode 211, and accordingly, the pressing pin 213 joined to the movable electrode 212 presses the liquid feed diaphragm 546 in a direction in which the volume of the liquid feed chamber 547 decreases. Thus, the internal pressure of the liquid chamber 547 is raised so that the outlet passage 20 which has been blocked by the outlet valve 544 is opened, and accordingly, the liquid is discharged from the discharge nozzle 214.

When the voltage applied between the stationary electrode 211 and the movable electrode 212 are cut off, the liquid diaphragm 546 is moved in a direction in which the volume of the liquid feed chamber 547 increases, by the restoring forces of the liquid feed diaphragm 546 and the liquid feed chamber 547 so that the internal pressure of the liquid feed chamber 547 decreases, and as a result, the outlet fluid resisting element 8 blocks the outlet passage 4 while the inlet flow passage 203 having blocked by the inlet valve 543 is opened. Thus, the liquid flows into the liquid feed chamber 547 through the fluid introduction port 202. With the repetitions of the above-mentioned operation steps, the liquid can be continuously fed.

It is noted that the characteristic of the inlet valve 543 is substantially the same as that of the outlet valve 544. This is because the resisting elements constituting the inlet and outlet ports, are formed in the second liquid feed substrate 205, and accordingly, in view of the manufacture thereof, they can be simply manufactured if they are fabricated from the same material as that of the second liquid feed substrate.

As the liquid is fed through the operation as mentioned above, the disadvantages of a conventional electrostatically driven micro-diaphragm pump, that is, the discharge pressure is low, can be eliminated, and accordingly, the cut-off of liquid in the discharge nozzle part can be improved in the case of discharge of the liquid into gas. It is noted that the responsiveness of the liquid feed diaphragm 546 can be improved with the provision of the resistance restraining groove 215 which decreases the resistance induced between the stationary electrode 211 and the liquid feed diaphragm 546, the quantity of the liquid fed by the diaphragm 546 through every operation can be decreased to a very small value, and the liquid feed diaphragm is driven at a high frequency so as to obtain a desired feed quantity of liquid, thereby it is possible to precisely control the liquid feed quantity.

Figure 9:
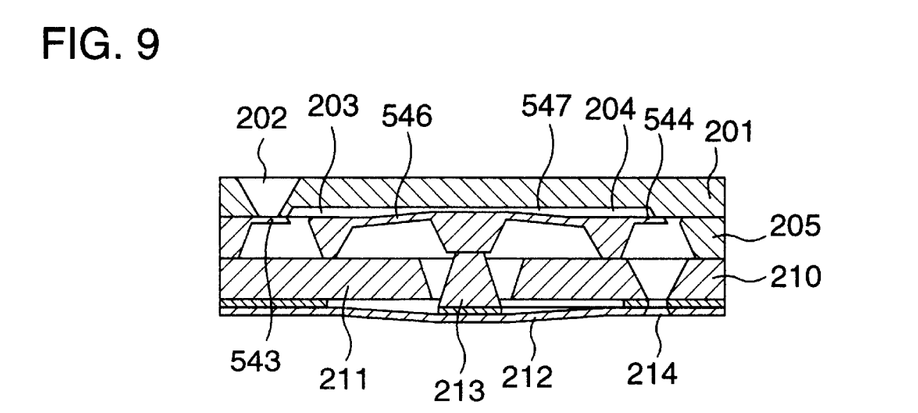
FIG. 9 is a sectional view illustrating a micropump in another embodiment of the present invention.

Referring to FIG. 9 which shows another example of the micropump, the micropump differs from the embodiment shown in FIG. 8 in view of the following point that the liquid feed diaphragm 546 is formed in a direction reverse to that in the embodiment shown in FIG. 8 in order to decrease the size of the liquid feed chamber 12, and a protrusion provided on the liquid feed diaphragm is pressed by the pressing pin 213 so as to discharge the liquid.

The liquid is fed as follows: a voltage is applied to the stationary electrode 211 and the movable electrode 212 which are joined together through the insulating film, so as to induce an electrostatic force by which the movable electrode 212 is attracted to the stationary electrode 211, and accordingly, the pressing pin 213 joined to the movable electrode 212 presses the liquid feed diaphragm 546 in a direction in which the liquid feed chamber 547 decreases its volume, and the internal pressure of the liquid feed chamber 547 is increased so as to open the outlet flow passage 204 which has been blocked by the outlet valve 544, and accordingly, the liquid is discharged from the discharge nozzle 214. When the voltage applied between the stationary electrode 211 and the movable electrode 212 is cut off, the diaphragm 546 is moved in a direction in which the volume of the liquid feed chamber 546 increases, by the restoring forces of the liquid feed diaphragm 546 and the movable electrode 212, and accordingly, the internal pressure of the liquid feed chamber 547 decreases so that the outlet valve 544 blocks the outlet passage 204 while the inlet passage which has been blocked by the inlet valve 543 is opened. Thus, the liquid flows into the liquid feed chamber 547 through the liquid introduction port 202. With the repetitions of the above-mentioned operational steps, the liquid can be continuously fed.

As the liquid is fed as mentioned above, the disadvantage of a conventional electrostatically driven micro-diaphragm pump, that is, the discharge pressure is low, can be eliminated, thereby it is possible to improve the cut-off of the liquid in the discharge nozzle part in the case of the discharge of the liquid into gas.

As mentioned above, the difference between this embodiment and the embodiment shown in FIG. 8 is such that the volume of the liquid feed chamber 547 is set to be small in this embodiment since the volume of the liquid feed chamber 547 is too large in comparison with the degree of deformation of the liquid feed diaphragm 546 in the embodiment shown in FIG. 8 so that the variation in pressure in the liquid feed chamber 547 caused by the deformation of the liquid feed diaphragm 546 is too small, resulting in that the fluid resisting element cannot be opened for introduction of the liquid. Accordingly, even though the liquid feed chamber is filled therein with gas, the liquid can be introduced into the micropump.

It is noted that the resistance between the first liquid feed substrate 201 and the liquid feed diaphragm 546 becomes large as the volume of the liquid feed chamber becomes small, and accordingly, a groove is formed in the surface of the first liquid substrate 201 facing the liquid feed diaphragm 546 so as to decrease the resistance as necessary. Further, when the liquid is introduced into the micropump, it is desirable to moderately drive the liquid feed diaphragm 546 at a drive frequency of less than 1 Hz.

Figure 10:
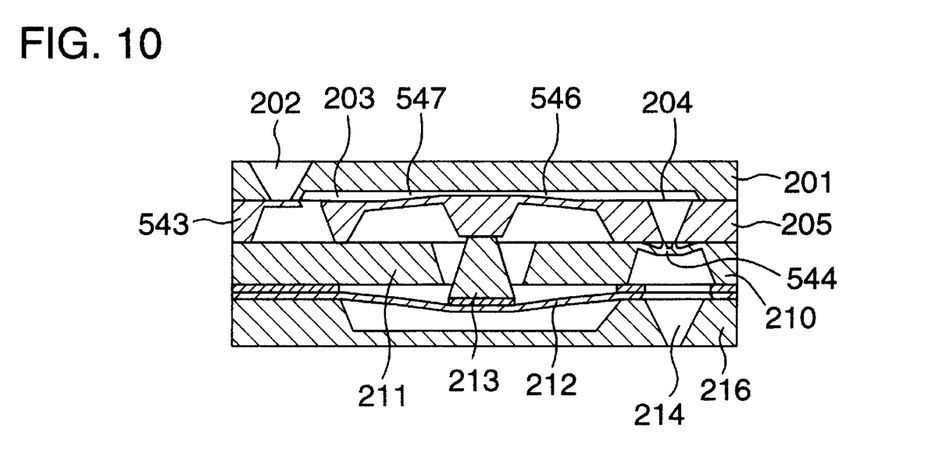
FIG. 10 is a sectional view illustrating a micropump in another embodiment of the present invention.

Referring to FIG. 10 which shows an another embodiment of the micropump, this embodiment differs from the embodiment shown in FIG. 9 in view of such a fact that the resistance of the inlet valve 543 is smaller than that of the outlet valve in this embodiment while the characteristics of the inlet valve and the outlet valve in the embodiment shown FIG. 9 are the same. Further, in this embodiment, the substrate 216 for the discharge nozzle is provided on the outside of the movable electrode 212 in order to protect the electrodes and improve the cut-out of the liquid in the discharge part.

The effects obtained by making the resistance values different from each other, are as follows: when the liquid is introduced into the micropump which is initially filled therein with, for example, gas, through the fluid introduction part 202, the beam in the form of the fluid resisting element cannot be opened by a variation in the pressure of the liquid feed chamber, caused by deformation of the liquid feed diaphragm 546, if the resistances of the inlet port and the outlet port are equal to each other, and accordingly, there would be presented such a case that the liquid cannot be introduced into the liquid feed chamber. Thus, the resistance of the inlet valve 543 against the inflow of the liquid in the inlet valve 543 is decreased to an extremely small value, and accordingly, the cantilever in the form of the inlet valve 543 is prevented from being made into close contact with the fluid introduction port 202 so as to hold a gap therebetween, through which the liquid can flow into the micropump from the level above the fluid introduction part 202 under potential energy alone if the liquid is present at the level.

At this time, if the resistance of the outlet valve becomes larger, the outlet valve 544 can be held to be closed so as to prevent discharge of the liquid until the liquid is filled in the micropump, and accordingly, the gas therein can be discharged into the liquid through the inlet port. Thus, the liquid can flows into the liquid feed chamber in place of the gas. Further, when the liquid is introduced into the micropump, it is desirable to moderately drive the liquid feed diaphragm at a frequency of less than 1 Hz.

Figure 11A:
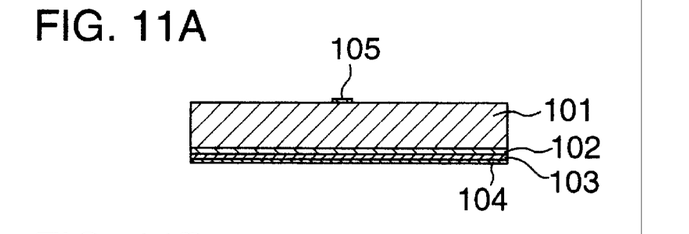
FIGS. 11a to 11f are views for explaining a process of manufacturing the micropump shown in FIG. 8.
Figure 11B:
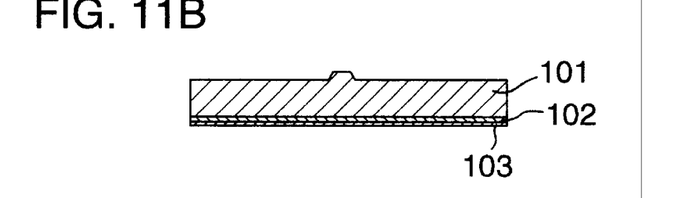
Figure 11C:
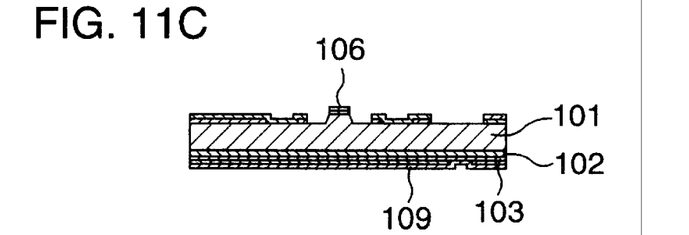
Figure 11D:
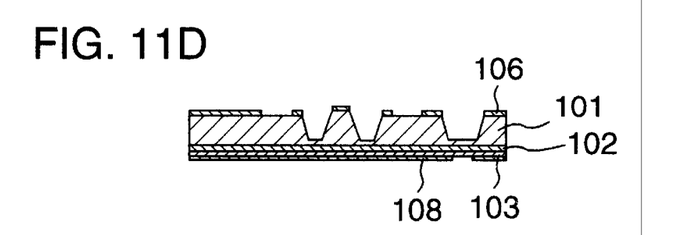
Figure 11E:
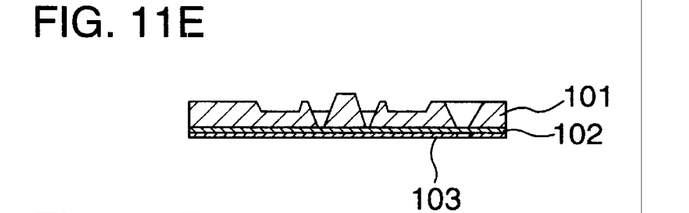
Figure 11F:
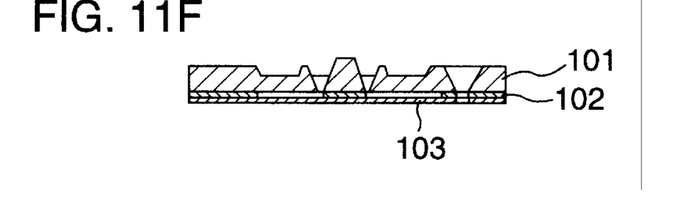

Next, explanation will be hereinbelow made of the method of manufacturing the drive part of the micropump shown in FIG. 8 with reference to FIGS. 11a to 11f. In this example, the drive part is made of an SOI (silicon on insulator) substrate. However, in general, it may be made of single crystal silicon substrates or glass substrates which are joined together. At first, at a step shown in FIG. 11a, etching masks 105, 104 for anisotropically etching a single crystal silicon substrate by alkali aqueous solution in order to form the pressing pin 213 shown in FIG. 1, are transcribed with the use of a thin film forming process or a photolithographing process so as to form a protrusion as shown in FIG. 11b. Etching masks 107, 109 for second etching adapted to separate the pressing pin 103 from the periphery surrounding therearound, and etching masks 106, 108 for the third etching adapted to form a resistance restraining groove 215 are formed being superposed with one another. At this time, the second and third masks are desirably made of selective different materials such as a silicon oxide film and a silicon nitride film. However, two etching masks made of the same material but having different film thickness may be used being superposed with each other. Next, the substrate is dipped in the alkali aqueous solution so as to carry out the second etching, and after the completion of the etching, the second etching masks 107, 109 are alone removed. Then the third anisotropic etching is carried out so as to obtain a desired silicon shape. Finally, the insulating film 103 interposed between the stationary electrode 211 and the movable electrode 212 is selectively removed so as to complete the manufacture of the drive part. It is noted that the necessity of the final step can be eliminated in the case of manufacturing the drive part with no use of the SOI substrate if a movable part of the movable electrode is prevented from sticking to the stationary electrode when the two substrates from which the stationary electrode and the movable electrode are formed are joined to each other.

According to the present invention, it is possible to provide a chemically analyzing apparatus incorporating a reagent supply mechanism which can prevent the reagent from being uselessly consumed, and which dose not require a substantial quantity of washing liquid, which does not also require periodical disassembly and washing, and which can easily change the feed quantity of the reagent.

What is claimed is:

1. A chemically analyzing apparatus comprising:
a reaction container holder for holding a plurality of reaction containers, and for moving said plurality of reaction containers to predetermined positions;
a plurality of reagent containers containing reagents therein, each of said plurality of reagent containers having a connection hole provided in a bottom surface;
a reagent container holder for holding said plurality of reagent containers;
a measuring part for measuring physical properties of said sample; and
a liquid feed mechanism having a fluid introduction part connected to said connection hole provided in the bottom surface of each of said plurality of reagent containers.

2. A chemically analyzing apparatus as set forth in claim 1, wherein an internal volume of said liquid feed mechanism extending from a suction port to a discharge port is less than 200 $\mu$L.

3. A chemically analyzing apparatus as set for in claim 1, wherein said liquid feed mechanism comprises a liquid feed chamber, a first fluid resisting member provided on an inlet port side of said liquid feed chamber, a second fluid resisting member provided on an outlet port side of said liquid feed chamber, a diaphragm in which at least one surface of said liquid feed chamber is deformable, and a drive mechanism for deforming said diaphragm, said drive mechanism comprising a stationary electrode and a movable electrode which are provided on one side of said diaphragm and
which are electrically insulated from each other, and a pressing member provided on said movable electrode, for driving said diaphragm.

4. A chemically analyzing apparatus as set forth in claim 3, further comprising:
a plurality of reagent container holders, each of said plurality of reagent container holders holding said plurality of reagent containers in a ring shape;
wherein said reaction container holder holds said plurality of reaction containers in a ring shape; and
wherein shifting loci of said plurality of reagent container holders cross locus of said reaction containers so that they are made into contact with each other at a one point, respectively, and reagent in said reagent containers are pipetted into the reaction container at said crossing points.

5. A chemically analyzing apparatus as set forth in claim 3, wherein said liquid feed mechanism is provided in each of said reagent holders, a port is formed in a bottom part of each of said reagent containers, and a removable seal is provided between opposed ports of said liquid feed mechanisms.

6. A chemically analyzing apparatus as set forth in claim 3, wherein said liquid feed mechanism is provided in a bottom part of each of said reagent containers.

7. A chemically analyzing apparatus as set forth in claim 3, wherein said liquid feed mechanism feeds a predetermined kind of reagent, each of said reagent containers incorporates in a part thereof a memory part for storing data as to a kind of reagent, said liquid feed mechanisms or the reagent holder incorporate a reading means for reading the data as to a kind of reagent stored in the memory part when or just after said reagent container is connected to said reagent holder, and there is provided a control mechanism which can perform connection if a kind of reagent read by said reading means coincides with a predetermined kind of reagent determined for each of said liquid feed mechanisms.

8. A chemically analyzing apparatus as set forth in claim 3, wherein an internal volume of said liquid feed mechanism extending from a suction port to a discharge port is less than 200 $\mu$L.

* * * * *